US00PP20703P2

(12) United States Plant Patent
Goemans

(10) Patent No.: US PP20,703 P2
(45) Date of Patent: Feb. 2, 2010

(54) ***ALSTROEMERIA* PLANT NAMED 'DAVINA'**

(50) Latin Name: *Alstroemeria hybrida*
Varietal Denomination: Davina

(75) Inventor: Robert Adrian Goemans, Spalding (GB)

(73) Assignee: Wülfinghoff Alstroemeria B.V., Rijswijk (NL)

( * ) Notice: Subject to any disclaimer, the term of this patent is extended or adjusted under 35 U.S.C. 154(b) by 0 days.

(21) Appl. No.: 12/283,263

(22) Filed: Sep. 8, 2008

(51) Int. Cl.
*A01H 5/00* (2006.01)

(52) U.S. Cl. ..... Plt./309

(58) Field of Classification Search ..... Plt./309
See application file for complete search history.

(56) References Cited

OTHER PUBLICATIONS

UPOV ROM GTITM Computer Database, GTI Jouve Retrieval Software 2008/06 Ciation for 'Davina'.*

Viv Marsh Postal Plants Catalog, 22 pages; see 'Little Miss Davina' on p. 11. Available at: http://www.postalplants.co.uk/showplants.asp?species=Alstroemeria&name=latinname&alpha=A.*

* cited by examiner

*Primary Examiner*—Wendy C Haas
(74) *Attorney, Agent, or Firm*—C. A. Whealy

(57) ABSTRACT

A new and distinct cultivar of *Alstroemeria* plant named 'Davina', characterized by its compact and mounding plant habit; sturdy and strong plants; vigorous growth habit; salmon pink and yellow-colored flowers; and good garden performance.

2 Drawing Sheets

Botanical designation: *Alstroemeria hybrida.*
Cultivar denomination: 'Davina'.

BACKGROUND OF THE INVENTION

The present invention relates to a new and distinct cultivar of *Alstroemeria* plant, botanically known as *Alstroemeria hybrida*, grown typically as a potted garden *Alstroemeria,* and hereinafter referred to by the name 'Davina'.

The new *Alstroemeria* plant is a product of a planned breeding program conducted by the Inventor in Chichester, England. The objective of the breeding program is to create new compact potted garden *Alstroemeria* cultivars that have attractive foliage and flower coloration.

The new *Alstroemeria* plant originated from a cross-pollination made by the Inventor in Chichester, England in June, 2000, of a proprietary selection of *Alstroemeria hybrida* identified as code number T10, not patented, as the female, or seed, parent with a proprietary *Alstroemeria hybrida* selection identified as code number 465/1, not patented, as the male, or pollen, parent. The new *Alstroemeria* was discovered and selected by the Inventor as a flowering plant from within the progeny of the stated cross-pollination in a controlled greenhouse environment in Chichester, England in May, 2002.

Asexual reproduction of the new *Alstroemeria* by tissue culture in a controlled greenhouse environment in Chichester, England since October, 2004, has shown that the unique features of this new *Alstroemeria* are stable and reproduced true to type in successive generations.

SUMMARY OF THE INVENTION

The new *Alstroemeria* has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Davina'. These characteristics in combination distinguish 'Davina' as a new and distinct cultivar of *Alstroemeria:*

1. Compact and mounding plant habit.
2. Sturdy and strong plants.
3. Vigorous growth habit.
4. Large salmon pink and yellow-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are more compact than plants of female parent selection.
2. Plants of the new *Alstroemeria* have larger flowers than plants of the female parent selection.
3. Plants of the new *Alstroemeria* and female parent selection differ in flower color as plants of female parent selection have lilac pink-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* have smaller flowers than plants of the male parent selection.
3. Plants of the new *Alstroemeria* and the male parent selection differ in flower color as plants of the male parent selection have pale orange-colored flowers.

Plants of the new *Alstroemeria* can be compared to plants of the *Alstroemeria hybrida* 'Natalie', disclosed in U.S. Plant Pat. No. 17,801. In side-by-side comparisons conducted in Chichester, England, plants of the new *Alstroemeria* differed from plants of 'Natalie' in the following characteristics:

1 Plants of the new *Alstroemeria* had larger flowers than plants of 'Natalie'.
2. Plants of the new *Alstroemeria* and 'Natalie' differed in flower color as plants of 'Natalie' had red and white-colored flowers.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Davina' grown in a container.

The photograph on the second sheet is a close-up view of typical flowers of 'Davina'.

DETAILED BOTANICAL DESCRIPTION

The aforementioned photographs and following observations and measurements describe plants of the new *Alstroemeria* grown in Chichester, England during the summer in a glass-covered greenhouse in 16-cm containers. During the production of the plants, day temperatures averaged 20° C. and night temperatures averaged 14° C. Plants used for the photographs and description had been growing for six months. Color references are made to The Royal Horticultural Society Colour Chart, 2001 Edition, except where general terms of ordinary dictionary significance are used.

Botanical classification: *Alstroemeria hybrida* 'Davina'.

Parentage:

*Female, or seed, parent.*—Proprietary selection of *Alstroemeria hybrida* identified as code No. T10, not patented.

*Male or pollen parent.*—Proprietary selection of *Alstroemeria hybrida* identified as code No. 465-1, not patented.

Propagation:

*Type.*—By tissue culture.

*Root description.*—Fleshy; color, close to 155A.

*Rooting habit.*—Moderate branching; dense.

*Rhizome description.*—Shape: Elongate; rounded. Length: About 6 cm. Diameter: About 1.1 cm. Texture: Smooth. Color: Close to 155A.

Plant description:

*Plant habit.*—Compact and mounded; freely branching, bushy appearance. Sturdy and strong plants; vigorous growth habit.

*Plant height.*—About 16 cm.

*Plant diameter* (*area of spread*).—About 27 cm.

Stem description:

*Aspect.*—Mostly upright to outwardly spreading.

*Internode length.*—About 0.2 cm to 2.5 cm.

*Strength.*—Strong, sturdy.

*Texture.*—Smooth, glabrous.

*Color.*—Close to 146C.

Foliage description:

*Arrangement.*—Alternate; below the peduncles in a single whorl; sessile.

*Length.*—About 5 cm to 5.5 cm.

*Width.*—About 1.8 cm to 2.3 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to 144B. Developing leaves, lower surface: Close to 144A. Fully expanded leaves, upper surface: Close to 144A; venation, close to 144A. Fully expanded leaves, lower surface: Close to 137B; venation, close to 138B.

Flower description:

*Flower type and habit.*—Single cup-shaped flowers arranged in compound umbels. Flowers face mostly upright to outwardly. Perianth segments separate. Freely flowering habit; about five to twelve flowers per inflorescence; about 120 flowers develop per plant.

*Natural flowering season.*—Flowering continuous from the late spring until frost in The Netherlands.

*Fragrance.*—None detected.

*Flower longevity on the plant.*—About two to three weeks on the plant; about one to two weeks as a cut flower; flowers not persistent.

*Flower buds.*—Length: About 4.7 cm. Diameter: About 1.8 cm. Shape: Ovoid. Color: Close to 34A; towards the apex, close to 143B.

*Flower diameter.*—About 7.5 cm.

*Flower depth* (*height*).—About 6 cm.

*Perianth.*—Arrangement: Six arranged in two whorls, each whorl with two lateral and one median segments. Size, inner perianth: Length, lateral segments: About 5.5 cm. Width, lateral segments: About 1.6 cm. Length, median segment: About 5 cm. Width, median segment: About 1.6 cm. Size, outer perianth: Length, lateral segments: About 5.5 cm. Width, lateral segments: About 3 cm. Length, median segment: About 6 cm. Width, median segment: About 3 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner perianth, lateral and median segments: Attenuate. Base, outer perianth, lateral and median segments: Cuneate. Margin, inner perianth, lateral and median segments: Entire. Margin, outer perianth, lateral and median segments: Slightly crenate. Texture, inner and outer perianths, lateral and median segments: Smooth, glabrous. Color, inner perianth: When opening, lateral and median segments, upper surface: Close to 14C; towards the apex, close to 51A; stripes, close to 184A. When opening, lateral and median segments, lower surface: Close to 16B; towards the apex, close to 51B; stripes, close to 177B. Fully opened, lateral and median segments, upper surface: Close to 16C; towards the apex, close to 51D; stripes, close to 177B. With development, color becoming closer to between 14C and 16C. Fully opened, lateral and median segments, lower surface: Close to 16D; towards the apex, close to 51B; stripes, close to 177D. Color, outer perianth: When opening, lateral and median segments, upper surface: Close to 51B; mid-section, close to 51A. When opening, lateral and median segments, lower surface: Close to 54B; stripes, close to 144A. Fully opened, lateral and median segments, upper surface: Close to 48C; mid-section, close to 48B. With development, color becoming closer to 51B. Fully opened, lateral and median segments, lower surface: Close to 53A; stripes, close to 144A.

*Pedicels.*—Length: About 2 cm. Diameter: About 2 mm. Strength: Strong. Angle: About 15° C. from vertical. Texture: Smooth, glabrous. Color: Close to 144B.

*Reproductive organs.*—Stamens: Quantity per flower: Six. Anther shape: Oval. Anther size: About 4 mm by 7 mm. Anther color: Close to N163C. Pollen amount: Abundant. Pollen color: Close to 15C. Pistils: Quantity per flower: One. Pistil length: About 3.5 cm. Style length: About 2.9 cm. Style color: Close to 11C. Stigma color: Close to 50B. Ovary color: Close to 143B.

*Fruits.*—Length: About 1.4 cm. Diameter: About 1.1 cm. Color: Close to 144A.

*Seeds.*—Seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures ranging from about 2° C. to about 25° C.

It is claimed:

1. A new and distinct *Alstroemeria* plant named 'Davina' as illustrated and described.

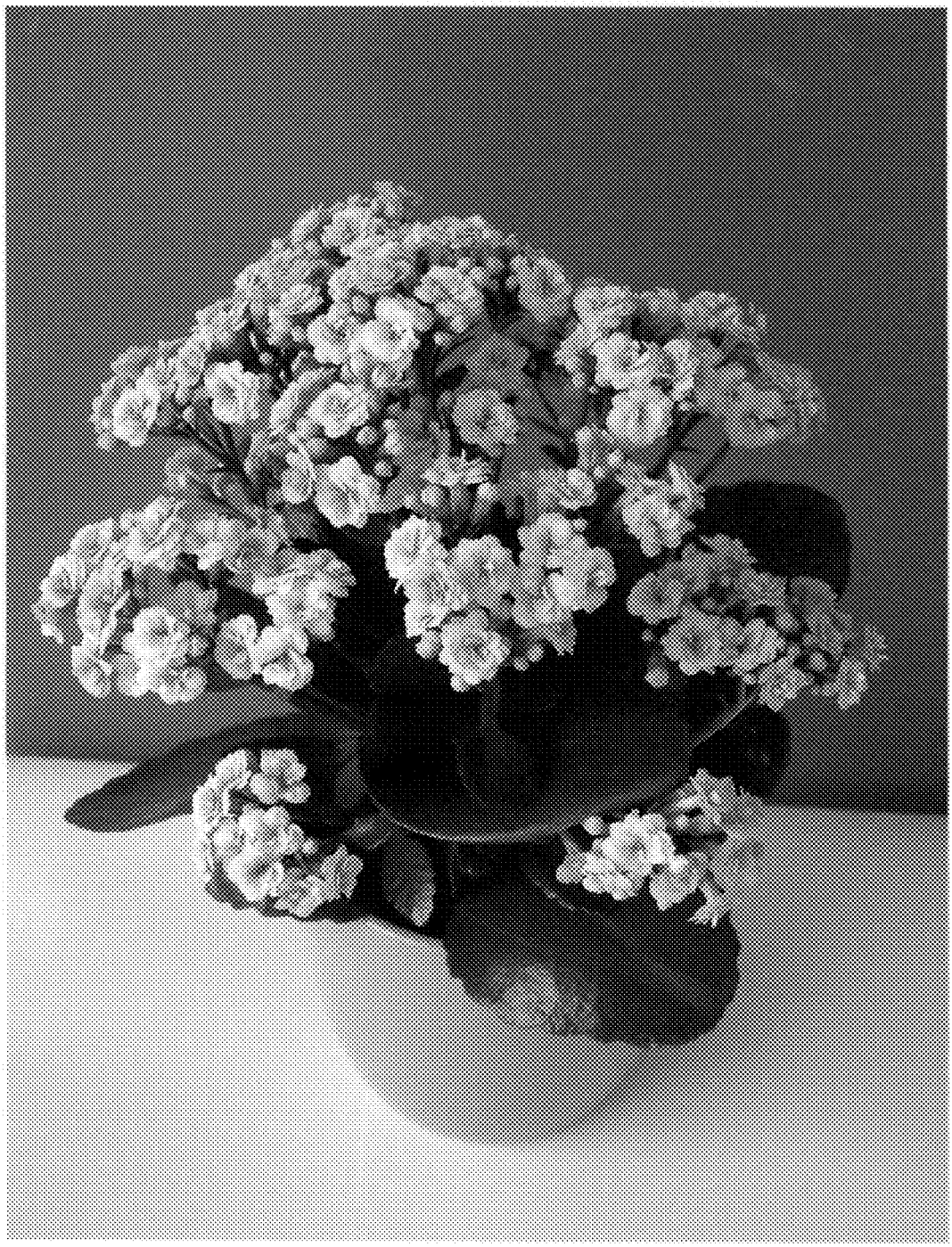

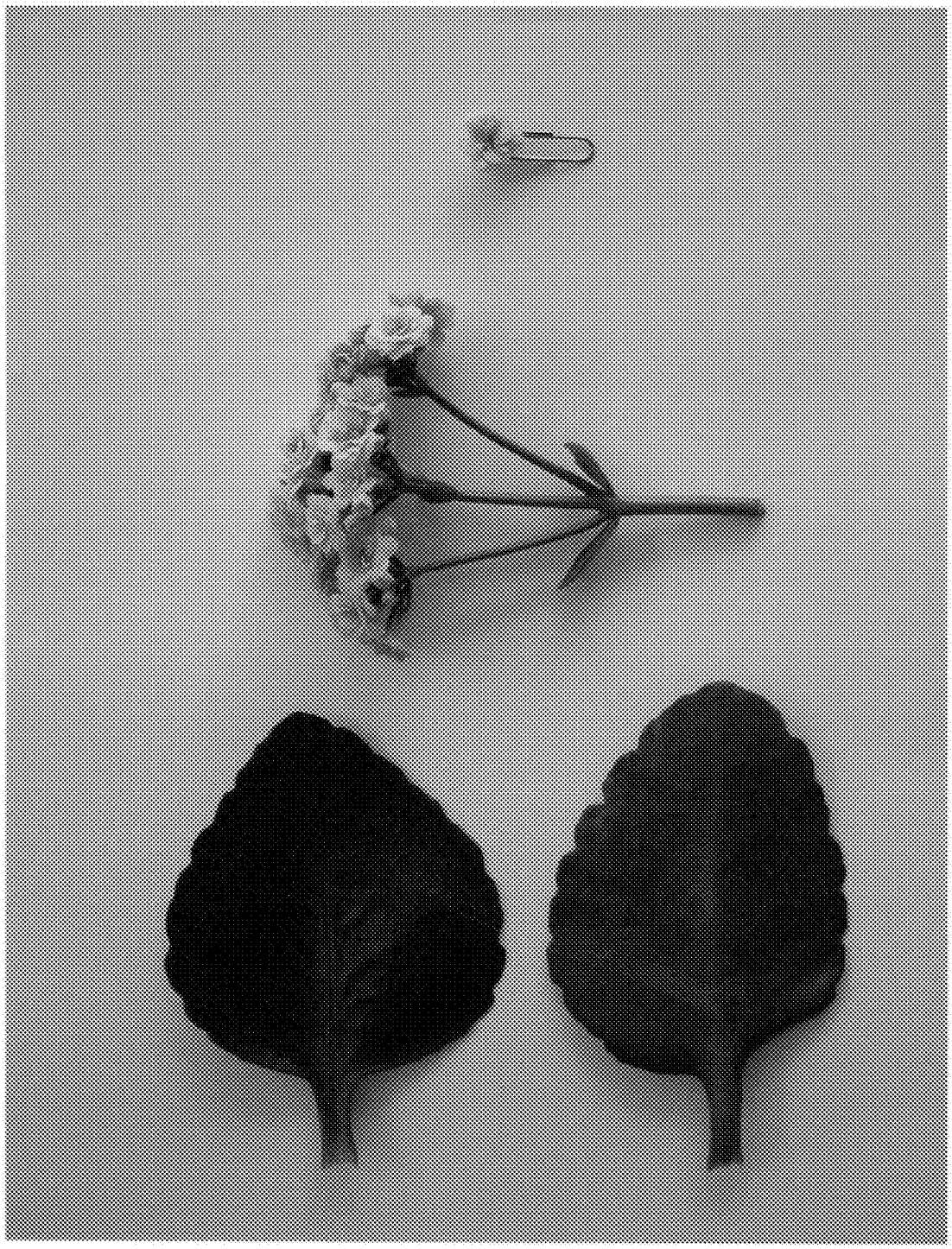

* * * * *